United States Patent [19]

Hurd et al.

[11] Patent Number: 4,618,147
[45] Date of Patent: Oct. 21, 1986

[54] BOWLING GLOVE

[75] Inventors: Bruce Hurd, Ridgefield, Conn.; Robert Oda, Englewood Cliffs, N.J.

[73] Assignee: AccuSwing, Incorporated, Easton, Conn.

[21] Appl. No.: 751,009

[22] Filed: Jul. 2, 1985

[51] Int. Cl.$^4$ ............................................. A63B 71/02
[52] U.S. Cl. ................................. 273/54 B; 128/88; 273/189 A
[58] Field of Search .................. 273/54 B, 189 A; 2/161 A; 128/88

[56] References Cited

U.S. PATENT DOCUMENTS

| | | | |
|---|---|---|---|
| 1,643,850 | 9/1927 | Jones | 128/88 |
| 3,033,567 | 5/1962 | Raab | 273/54 B |
| 3,117,786 | 1/1964 | Anderson | 273/54 |
| 3,438,630 | 4/1969 | Petti | 273/54 B |
| 3,829,090 | 8/1974 | Ensinger | 273/54 |
| 3,975,015 | 8/1976 | Owens et al. | 273/54 |
| 3,994,493 | 11/1976 | Newman | 273/54 |
| 4,138,108 | 2/1979 | Robinson | 273/54 |
| 4,254,953 | 3/1981 | Marchetti | 273/54 |
| 4,336,796 | 6/1982 | Andrews | 128/87 |
| 4,371,163 | 2/1983 | Shaffer et al. | 273/54 |
| 4,441,711 | 4/1984 | Dubar | 273/54 |

FOREIGN PATENT DOCUMENTS 2239760 8/1972 Fed. Rep. of Germany ........ 128/88

Primary Examiner—Anton O. Oechsle
Attorney, Agent, or Firm—Oltman and Flynn

[57] ABSTRACT

A bowler's adjustable wrist brace is made into a glove-like configuration. The brace enables the bowler to quickly and conveniently lock his wrist at various desired angles in order to control the "hook" or sidespin of the bowling ball. Bowling alley lane conditions vary. Even varying amounts of oil applied to the same lane can result in different paths for the same ball throw. This brace enables the bowler to adjust his wrist position for different lane conditions.. Additionally, the bowler may achieve a different amount of hook on the same alley for various shots by simply adjusting a lever. A calibrated wrist angle indicator enables the bowler to repeat various desirable wrist positions for his different shots.

2 Claims, 6 Drawing Figures

BOWLING GLOVE

BACKGROUND OF THE INVENTION

All bowlers must control their wrist position when rolling the bowling ball in order to maintain control of the ball. Ideally a controlled amount of hook or sidespin can increase the chances of a strike by directing the ball into the strike pocket on either side of the number one pin. When the same bowler wishes to shoot for a spare, he would want to make the ball travel in a straight path which in most cases makes the spare shot easier. The smallest angle between the wrist and forearm results in the largest hook. Therefore, an expert bowler must learn to control and lock his wrist into various positions for different shots. An easily adjustable wrist brace controlling the wrist to forearm angle with the capability of switching positions and returning to known positions would ideally assist the bowler. The present device combines a simple calibrated adjusting means with a rigid wrist brace with a simple Velcro ® strapping means to result in a practical and reasonably priced bowling aid.

SUMMARY OF THE INVENTION

The primary object of the present invention is to provide a calibrated adjustable wrist brace which can be quickly and easily adjusted to varying angles. This enables the bowler to adjust his path for various shots.

The secondary object of the present invention is to provide a comfortable and quickly donned brack that fits like a glove.

Other objects of this invention will appear from the following description and appended claims, reference being had to the accompanying drawings forming a part of this specification wherein like reference characters designate corresponding parts in the several views.

Note—All figures display a right-handed version of the device. A left handed version is substantially similar except for the reverse position of the lever and the different angular shape of the back of the hand brace for fitting a left hander.

DETAILED DESCRIPTION OF THE PREFERRED EMBODIMENT

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

Figure 1:
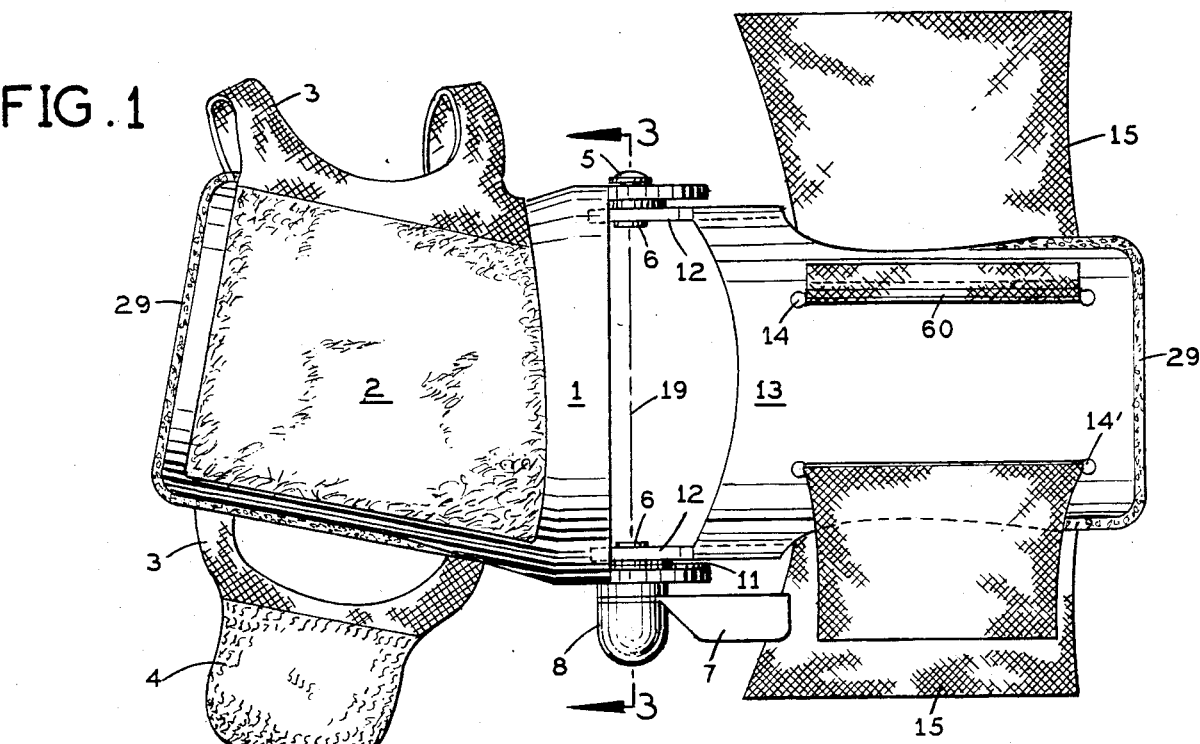
FIG. 1 is a top view displaying all the major components of the device.

Referring first to FIG. 1, two rigid shells, 1 and 13 comprise the structural wrist support. The back of the hand brace 1 is rigid and contoured concave against the hand. Forearm brace 13 is contoured concave against the forearm. Hand brace 1 secures to the hand by means of strap 3 and Velcro ® mats 2 and 4. Hand brace stiffening brackets 11 is riveted to the hand brace 1 to form a hinge 19 with forearm stiffening bracket 12 which is riveted to the forearm brace 13. The hinge 19 is comprised of pop rivets 5, tubular pivot pins 6, flat washers 6', friction plate 18, locking nut 8, washer 20, externally threaded stud 30 and locking lever 7 (see FIG. 3).

The forearm brace 13 is further comprised of strap fastening notches 14 and 14' and strap 15. Velcro ® mats 17 on strap 15 (see FIG. 5) cooperate to secure the forearm brace 13 to the forearm.

Figure 2:
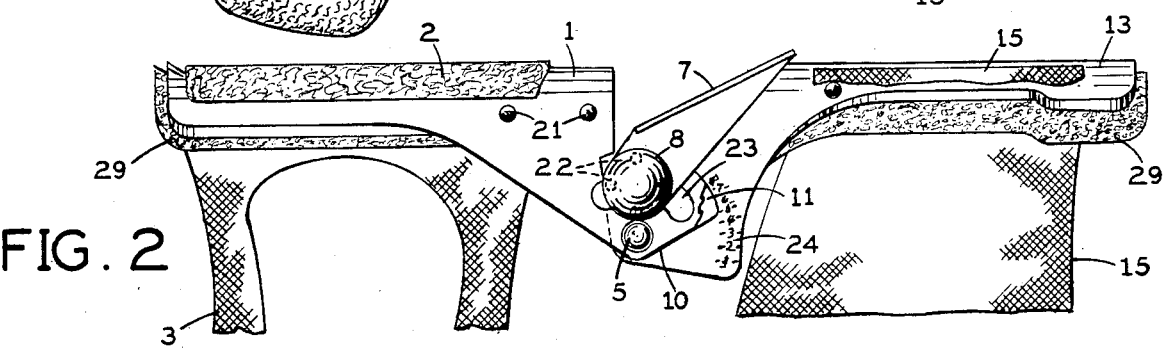
FIG. 2 is a side elevational view of the device displaying the calibrated scale.
Figure 3:
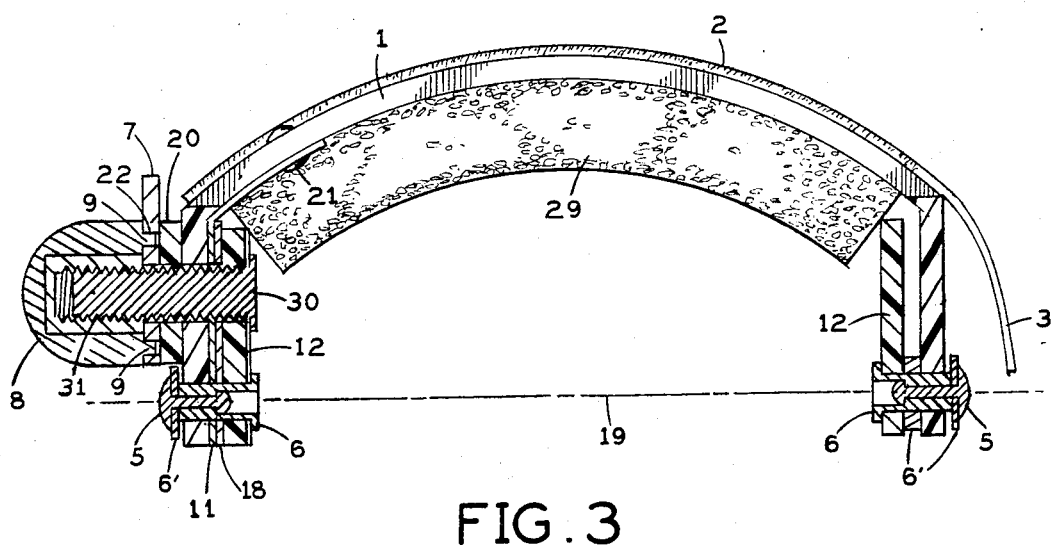
FIG. 3 is a cross-section of the hinge along line 3—3 of FIG. 1 looking forward toward the hand section of the device.

Referring to FIG. 2, foam pads 29 provide a comfortable fit against the body for braces 1 and 13. Stiffening rivets 21 for the hand brace stiffening bracket 11 are shown. Lever 7 can be adjusted to various positions by means of holes 22, and studs 9 (FIG. 4) which are part of locking nut 8. Stiffening bracket 11 pivots on pivot pin 6 (FIG. 3). Forearm stiffening bracket 12 has an externally threaded stud 30 attached (see FIG. 3) which slides in slot 23. Stud 30 presses into stiffening plate 12 (see FIG. 3). Calibration scale 24 on forearm brace 13 displays the desired angle of the hinge 19. Pushing lever 7 locks the hinge 19 at one angle by tightening locking nut 8 on stud 30 and thereby clamping stiffening bracket 12 to stiffening bracket 11 (see FIG. 3).

FIG. 3 shows the locking means for the hinge 19. Lever 7 turns locking nut 8 by means of studs 9 and holes 22 which in turn rotates locking nut 8 and tightens threads 31 of the locking nut 8 against matching threads 31 of the stud 30. Pivot pins 6 provide the main support for hinge 19.

Figure 4:
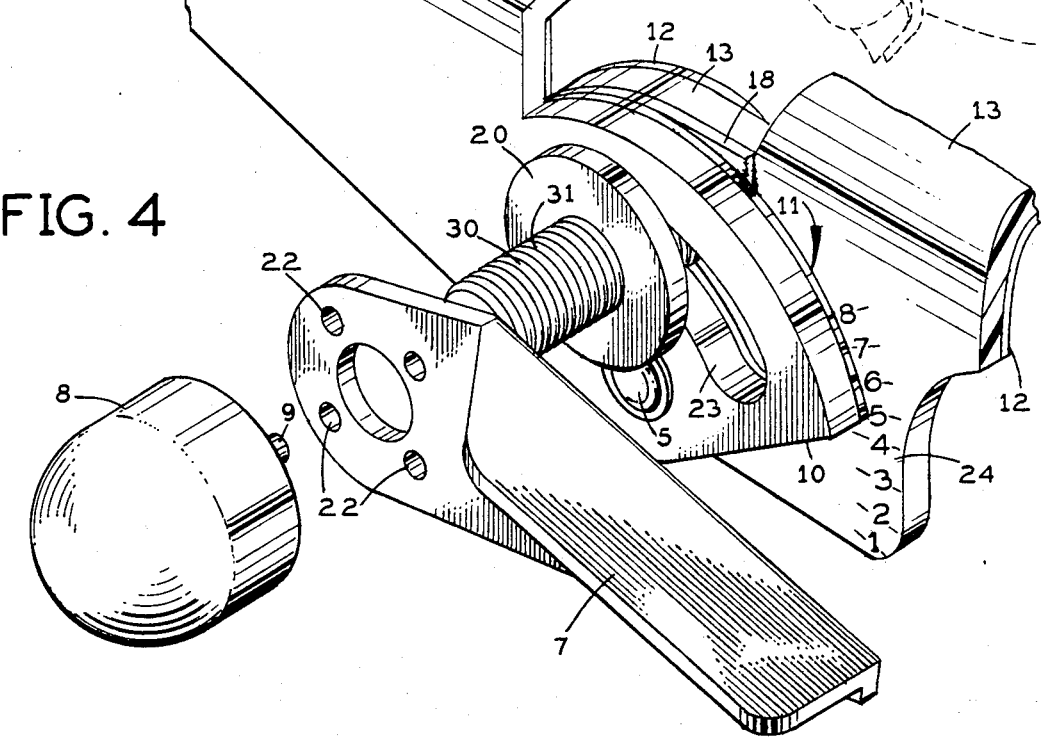
FIG. 4 is a detailed perspective of the hinge locking means and calibrated scale.

FIG. 4 provides a close-up view of calibrated scale 24 on forearm brace 13. Lever 7 can be adjusted to suit the user's preference by loosening locking nut 8 and positioning studs 9 in holes 22. Washer 20 and frictional plate 18 allow hand stiffening bracket 11 and hand brace 1 to rotate around forearm stiffening plate 12 and forearm brace 13 to obtain the desired setting on scale 24. The setting is determined by lining up edge 10 of hand brack 1 with calibration lines on scale 24.

Figure 5:
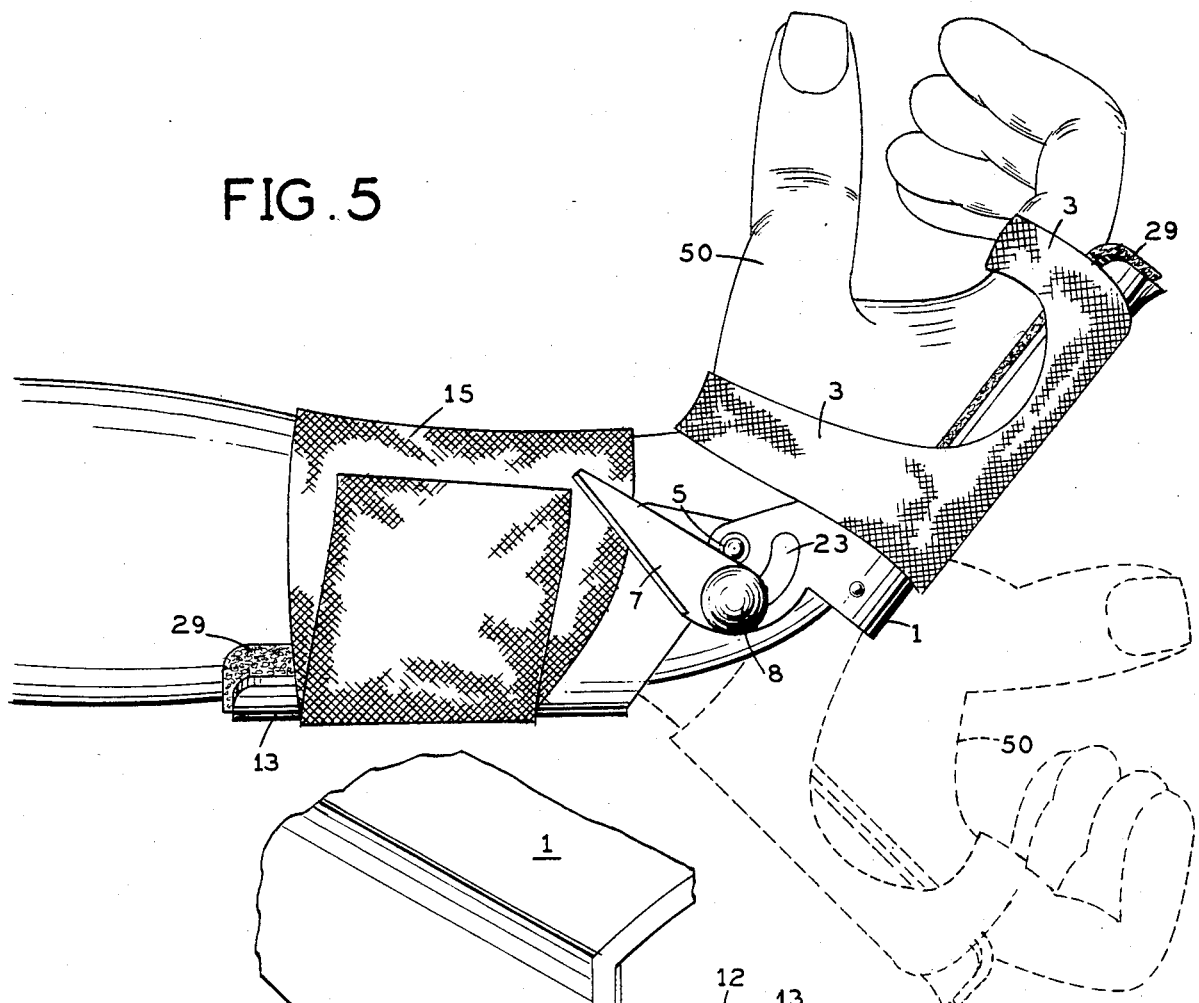
FIG. 5 is a side view of a bowler's hand in the device positioned in the two most extreme wrist angle positions.

FIG. 5 shows the bowler's hand 50 in its extreme most inward angle to provide maximum hook. By loosening locking nut 8 with lever 7 and moving the hand 50 to the extreme outward angle (shown in dots), the bowler can best roll a straight ball. The middle position encourages the bowler to roll a ball with moderate hook.

Figure 6:
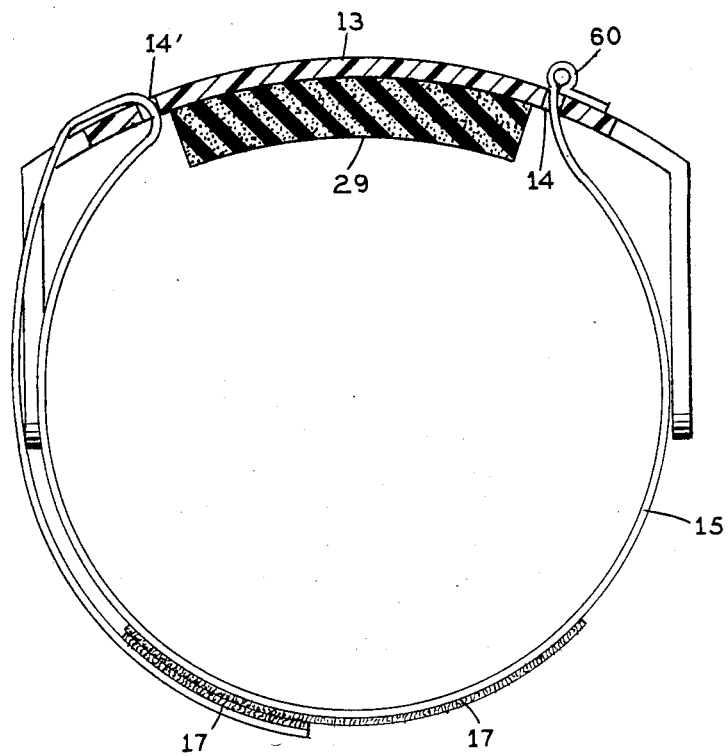
FIG. 6 is a cross-section of the forearm section of the device looking forward toward the hand section.

FIG. 6 shows how strap 15 is pulled around the foreasrm (not shown), through slot 14' before folding back over itself and fastening Velcro ® mats 17. Strap 15 is secured to forearm brace 13 by being folded once over itself and stitched along its width 60 after insertion into slot 14.

We claim:
1. A wrist brace for a bowler, comprising:
    a rigid support body for the back of the hand provided with a layer of resilient material between said support body and said bowler's hand;
    a rigid support body for the forearm provided with a layer of resilient material between said support body and said bowler's forearm;

a hinge acting between said rigid support bodies;

said hinge further comprising adjustable locking means functioning to allow said bowler to lock said brace at various angles;

said adjustable locking means further comprising a calibrated angle indicating scale;

strap means to secure said support bodies firmly but removably against said bowler's hand and forearm;

said adjustable locking means further comprising a bolt on the thumb side of said wrist brace projecting through said rigid body supports for the back of the hand and forearm, and having a locking nut projecting outward from said wrist brace;

said locking nut further comprising an adjustable lever for tightening around said bolt, wherein said locking nut further comprises at least one stud slidingly engaged into various holes in said adjustable lever functioning to allow the adjustable lever to lock together said rigid body supports for the back of the hand and forearm; and said calibrated angle indicating scale further comprising angle indicating lines marked onto said rigid support body for the forearm cooperating with a calibrated edge of said rigid support body for the back of the hand, wherein the bowler can easily see the wrist brace angle on the locking nut side while tightening said locking nut to the desired angle by means of said adjustable lever.

2. The wrist brace of claim 1, wherein said hinge further comprises a pivot line coincident with the bowler's wrist joint, thereby functioning to provide comfort and natural wrist flexing for the bowler.

* * * * *